United States Patent
Flores Oropeza et al.

(10) Patent No.: US 9,752,084 B2
(45) Date of Patent: Sep. 5, 2017

(54) BLOCK COPOLYMERS, SYNTHESIS AND APPLICATION AS DEHYDRATING AND DESALTING OF HEAVY CRUDES

(71) Applicant: INSTITUTO MEXICANO DEL PETROLEO, Mexico City (MX)

(72) Inventors: Eugenio Alejandro Flores Oropeza, Mexico City (MX); Cesar Andres Flores Sandoval, Mexico City (MX); Reyna Reyes Martinez, Mexico City (MX); Jose Gonzalo Hernandez Cortez, Mexico City (MX); Alfonso Lopez Ortega, Mexico City (MX); Laura Veronica Castro Sotelo, Mexico City (MX); Fernando Alvarez Ramirez, Mexico City (MX); Arquimedes Estrada Martinez, Mexico City (MX); Flavio Salvador Vazquez Moreno, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 532 days.

(21) Appl. No.: 14/189,309

(22) Filed: Feb. 25, 2014

(65) Prior Publication Data
US 2014/0238900 A1    Aug. 28, 2014

(30) Foreign Application Priority Data
Feb. 26, 2013    (MX) .................... MX/a/2013/002243

(51) Int. Cl.
*C10G 33/04*    (2006.01)
*C10G 31/08*    (2006.01)

(52) U.S. Cl.
CPC ............. *C10G 33/04* (2013.01); *C10G 31/08* (2013.01)

(58) Field of Classification Search
CPC ................................. C10G 33/04; C10G 31/08
See application file for complete search history.

(56) References Cited

U.S. PATENT DOCUMENTS 8,815,960 B2 *  8/2014  Cendejas Santana ................... C08G 65/33306
                                                                           208/188
2009/0259004 A1  10/2009  Newman et al.
(Continued)

FOREIGN PATENT DOCUMENTS

MX    MX/a/2008/015756    12/2008
MX    MX/a/2011/003848    4/2011
(Continued)

OTHER PUBLICATIONS

Atta, A. et al., Demulsification of crude oil emulsions using some new water-soluble Schiff base surfactant blends, Journal of Dispersion Science and Technology, 29:1484-1495, 2008.
(Continued)

*Primary Examiner* — Randy Boyer
*Assistant Examiner* — Juan Valencia
(74) *Attorney, Agent, or Firm* — Dickinson Wright PLLC

(57) ABSTRACT

The present invention is related to formulations consisting by block copolymers α,ω-di-aryl or alkyl sulfonates of poly(ethylene oxide)$_w$-poly(propylene oxide)-poly(ethylene oxide)$_w$ of bis-ammonium and block copolymers α,ω-di-amine of poly(ethylene oxide)$_w$-poly(propylene oxide)-poly(ethylene oxide)$_w$, that are effective in the dewatering and desalting crude whose specific gravities are within the range of 14 to 23° API.

5 Claims, 10 Drawing Sheets

(56) References Cited

U.S. PATENT DOCUMENTS

2009/0306232 A1 12/2009 Williams
2010/0140141 A1 6/2010 Cendejas Santana et al.

FOREIGN PATENT DOCUMENTS

MX MX/a/2011/004120 4/2011
WO 2007/115980 10/2007

OTHER PUBLICATIONS

Abdel-Azim, A. et al., Polyoxyalkylenated amines for breaking water-in-oil emulsions: Effect of structural variations on the demulsification efficiency, Polymers for Advanced Technologies, 9, 159-166 (1998).
Peng, J.X. et al., Novel magnetic demulsifier for water removal from diluted bitumen emulsion, Energy Fuels 2012, 26, 2705-2710.
Mirvakili, A. et al., Effect of a cationic surfactant as a chemical destabilization of crude oil based emulsions and asphaltene stabilized, J. Chem. Eng. Data 2012, 57, 1689-1699.
Feng, J. et al., Dilational viscoelasticity of the zwitterionic gemini surfactants with polyoxyethylene spacers at the interfaces, Journal of Dispersion Science and Technology, 32:1537-1546, 2011.

* cited by examiner

BLOCK COPOLYMERS, SYNTHESIS AND APPLICATION AS DEHYDRATING AND DESALTING OF HEAVY CRUDES

CROSS-REFERENCE TO RELATED APPLICATION

This application claims the benefit and priority to Mexican application No. MX/a/2013/002243 with a filing date of Feb. 26, 2013, the disclosure of which is incorporated herein by reference in its entirely.

FIELD OF THE INVENTION

This invention is related with the synthesis of basic chemicals to break up several kinds of water-oil emulsions and decrease its salt content. The invention is further directed to the synthesis of new copolymers block $\alpha,\omega$-bifunctionalized with tertiary amines (aliphatic and aromatic) and their individual application and formulation as dehydrating and desalting agents in crude oils with 14-23° API.

BACKGROUND OF THE INVENTION

The extraction of crude oil from reservoirs involves formation of water in crude oil emulsions, crude oil in water emulsions and tertiary emulsions water/crude oil/water and crude oil/water/crude oil. Such emulsions are produced by the turbulence promoted by the pumping power used in wells. These emulsions can be very stable and their formation is favored and stabilized by compounds naturally present in crude oil such as clays, naphthenic acids, rusty hydrocarbon and asphaltene. The water emulsified in crude oil contains inorganic salts; mostly sodium, magnesium, calcium chlorides, carbonates and sulfates; and iron sulfides and oxides. If not removed, these salts may cause various problems of corrosion and scaling in all the subsequent refining process (piping, storage tanks, distillation columns, heat exchangers, catalysts, piping systems, etc.). Additionally, the produced crude oil must comply with international quality standards relating to the maximum content of salt and water, for possible export [1].

Therefore, from an economic point of view, it is imperative and important to separate water from crude oil and simultaneously reduce the salt content.

Since the last century, different chemical products have been used to carry out the demulsification process of water in crude oil. The water is commonly added as formulations consisting of groundbreaking agents, coalescing and emulsion clarifiers. The nature of these products are polymeric.

Examples of polymeric formulations include alkoxylated alkylphenol resins formaldehyde [2], alkoxylated epoxy resins [2], block copolymers of polyoxyethylene-polyoxypropylene-polyoxyethylene (POE-POP-POE) and polyoxypropylene-polyoxyethylene-polyoxypropylene (POP-POE-POP), using various initiators such as propylene glycol or ethylenediamine [3], polyethers, polyesters and/or polyurethanes, polyesters together by dicarboxylic acids and/or diisocyanates [4], aliphatic and aromatic anhydrides in combination with glycolic esterified resins [5], ethyl cellulose on nano magnetic particles crosslinked in combination with the application of external magnetic fields [6], cationic surfactants [7], symmetric type surfactants with polyoxyethylene spacers fragments [8] among some others.

The Mexican Petroleum Institute (Research Program in Molecular Engineering) proposed innovative solutions to the problem of dehydrating and desalting of crude oils, resulting in four patent applications in this specific area. The formulations used triblock type copolymers poly(ethylene oxide)-poly(propylene oxide)-poly(ethylene oxide) which were bifunctionalized with amines to dehydrate heavy crude oils, achieving water removal 30 to 80% and salts of heavy crude oils 30-65% [9-10]. Another method uses ionic liquids individually and formulations for dehydrating and desalting medium, heavy and extra heavy crude oils (API gravities between 8 and 20) where dehydrating and desalting efficiencies reached about 90% and 76%, 90% and 71%, 90% and 71%, respectively. The addition of additives was done in concentrations between 50 and 2000 ppm [11]. Another method involves the application of synergistic formulations of ionic liquids (IL's) and formulations of triblock copolymers (CF's) $\alpha,\omega$-bifunctionalized with amines of ethylene polyoxide-propylene polyoxide-ethylene polyoxide, each individually or in formulation, in crude oils whose gravities are between 9 and 30° API [12].

REFERENCES

[1] Atta A M, Abdel Rahman A A H, Elsaeed S M, AbouElfotouh S, Hamad N A. Demulsification of crude oil emulsions using some new water-soluble Schiff base surfactants blends. J. Disp. Sci. Technol. 2008; 29: 1484-1495.

[2] Hellberg P E, Uneback I. Environmentally-friendly oil/water demulsifier. Patent WO 2007/115980.

[3] Abdel-Azim A A A, Zaki N N, Maysour, N E S. Polyoxyalkylenated amines for breaking water-in-oil emulsions: Effect of structural variations on the demulsification efficiency. Polymer. Adv. Technol. 1998; 9: 159-166.

[4] Newman S P, Hahn C and McClain R D Environmentally friendly demulsifiers for crude oil emulsions. US 2009/0259004.

[5] Williams D E. Anhydride demulsifier formulations for resolving emulsion of water and oil. US 2009/0306232.

[6] Peng J X, Liu Q X, Xu Z H, Masliyah J. Novel magnetic demulsifier for water removal from diluted bitumen emulsion. Energy Fuels 2012; 26:2705-2710.

[7] Mirvakili A, Rahimpour M R, Jahanmiri A. Effect of a cationic surfactant as a chemical destabilization of crude oil based emulsions and asphaltene stabilized. J. Chem. Eng. Data 2012; 57:1689-1699.

[8] Feng J, Liu X P, Zhang L, Zhao S, Yu J Y. Dilational viscoelasticity of the zwitterionic Gemini surfactants with polyoxyethylene spacers at the interfaces. J. Disp. Sci. Technol. 2011; 32:1537-1546.

[9] Cendejas G, Flores E A, Castro L V, Estrada A, Lozada M, Vázquez F S (2008) Formulaciones desemulsificantes y deshidratantes para crudos pesados a base de copolímeros en bloques bifuncionalizados con aminas, Mx/a/2008/015756.

[10] Cendejas G, Flores E A, Castro L V, Estrada A, Lozada M, Vazquez F S (2010) Demulsifying and dehydrating formulations for heavy crude oils base on block copolymers bifunctionalized with amines, US 2010/0140141 A1

[11] Flores E A, Castro L V, López A, Hernández J G, Alvarez F, Vázquez F S, Estrada A, Lozada M. Deshidratación y desalado de crudos medios, pesados y extrapesados utilizando líquidos iónicos y sus formulaciones. Solicitud de patente mexicana (IMP-959, MX/a/2011/003848).

[12] Flores E A, Castro L V, López A, Hernández J G, Alvarez F, Estrada A, Vázquez F S, Formulaciones sinérgicas de copolímeros funcionalizados y líquidos ionicos para el deshidratado y desalado de aceites crudos medianos, pesados y extrapesados. (IMP-953, Mx/a/2011/004120).

These documents are hereby incorporated by reference in their entirety.

SUMMARY OF THE INVENTION

In the present invention, new compounds are synthesized as demulsifiers from block copolymers of poly(ethylene oxide)-poly(propylene oxide)-poly(ethylene oxide) which are α,ω-bifunctionalized with tertiary amines (aliphatic and aromatic). The compounds are evaluated individually in the dehydrating of different types of crude oils or blends, achieving efficiencies of dehydrating or desalting (78-100%) and (65-91%), respectively which outperforms the prior processes.

The present invention is also directed to a method of dewatering, desalting and breaking emulsions in crude oil and particularly heavy crude oil of 14-23° API. The method comprises the steps of adding an effective amount of one or more α,ω-bifunctionalized poly(ethylene oxide)-poly(propylene oxide)-poly(ethylene oxide) copolymer that is functionalized with aliphatic or aromatic tertiary amines. The triblock copolymers have a polydispersibility of 1.02 to 1.20 and have a molecular weight of 1000 to 4000 Daltons. The copolymers are added in an amount of about 200 to 2000 ppm based on the amount of the crude oil. In other embodiments, the copolymer can be used in amounts of about 150 to 15000 ppm, and preferably about 200 to 1000.

The present invention is also directed to desalting and dewatering agents and formulations of the block copolymers in solvents or carriers. The formulations are then added to and mixed with the crude oil in an amount of provide an effective amount of the copolymers to dehydrate and desalinate the crude oil. The formulations can contain one of the block copolymers or mixtures of two or more of the block copolymers.

The process of making the copolymer basically reacts an α,ω-dialkyl or α,ω-diaryl-sulfonate ester of poly(ethylene oxide)-poly(propylene oxide)-poly(ethylene oxide) with an aliphatic or tertiary amine. The polyalkylene oxide typically has a molecular weight of about 1200-4500 g/mol and a polydispersibility of 1.11-1.15.

The method of demulsifying, dehydrating and desalination of crude can be by mixing a composition or formulation with heavy crude oil. The composition or formulation can be added in an amount of about 0.01% to about 5% by weight to provide a concentration of about 100 to 6000 ppm of the total amount of the copolymers based on the amount of crude oil. The formulation can comprise a mixture of two or more of the copolymers. Mixtures of the copolymers can be added where each is included in amounts of about 100 to 300 ppm, and preferably about 200 to 300 ppm based on the amount of crude oil.

In one embodiment of the invention, a combination of at least two of the copolymers is mixed with crude oil. It has been found that a combination of two copolymers provide a synergistic effect compared to when the copolymers are used alone in corresponding equivalent total amounts of the copolymers. In various embodiments of the invention, the copolymers can be used as a mixture of two chinolinium-modified copolymers, a mixture of an alkyl-modified copolymer with a chinolinium-modified copolymer, a mixture of an imidazolium-modified copolymer and a chinolinium-modified copolymer, and a mixture of an alkyl-modified copolymer and an imidazolium-modified copolymer.

The dewatering and desalting agents and formulations of the invention can include a mixture of two copolymers in a ratio of about 1:1. The mixtures of the copolymers can be a mixture of a copolymer of Formula 1 and a copolymer of Formula 2, a mixture of a copolymer of Formula 1 and at least one copolymer of Formula 3 or Formula 4, a mixture of a copolymer of Formula 2 and at least one copolymer of Formula 3 or Formula 4, a mixture of a copolymer of Formula 2 and a copolymer of Formula 5, and a mixture of a copolymer of Formula 1 and a copolymer of Formula 5.

BRIEF DESCRIPTION OF THE DRAWINGS

The figures of this application are graphic showing the results of the assessment of the dewatering and desalting activity of crude oil by the addition of the block copolymers α,ω-bifunctionalized with tertiary amines (aliphatic and aromatics), individually and in a formulation containing the copolymers. In these examples, the crude oil has gravities in the range of 14-23° API. In addition, the results of a commercial formulation so-called IMP-RHS-5 are included.

DETAILED DESCRIPTION OF THE INVENTION

Figure 1:
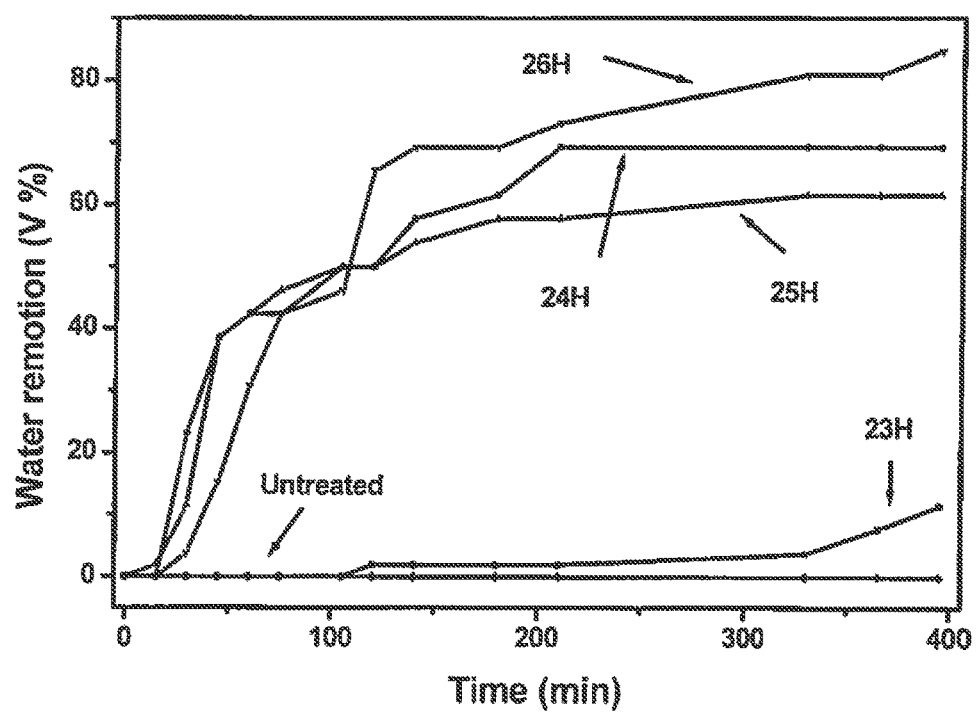
FIG. 1 is a graph showing the demulsifying activity of (23H-26H) triblock copolymers α,ω-bifunctionalized with tertiary amines, on CM1 crude oil at 80° C. and 600 ppm.

The present invention relates to the synthesis of novel block copolymers with low polydispersity like poly(ethylene oxide)-poly(propylene oxide)-poly(ethylene oxide), using ethylene glycol as initiator, and where the copolymers are α,ω-bifunctionalized with tertiary amines (aliphatic and aromatic). The efficiency of the above copolymers is attributed to having a polydispersity of about 1.02 to 1.20, the bifunctionalization with tertiary amines (aliphatic and aromatic) and molecular weights in the range of 1000 to 4000 Daltons, and preferably 1200 to 2700 Daltons.

The experimental process development for synthesizing the above-described compounds, consisted in the following three steps:
1. Synthesis of poly(oxyethylene)$_w$-poly(oxypropylene)$_y$-poly(oxyethylene)$_w$ block copolymers. In one embodiment, the alkylene oxide has the formula R discussed below.
2. Alkyl and aryl sulfonation of the terminal α,ω-hydroxyl groups of the poly(oxyethylene)$_w$-poly(oxypropylene)$_y$-poly(oxyethylene)$_w$ block copolymers.
3. Nucleophilic substitution of α,ω-alkyl and arylsulfonates of poly(oxyethylene)$_w$-poly(oxypropylene)$_y$-poly(oxyethylene)$_w$ block copolymers with tertiary amines (aliphatics and aromatics).

One method of producing block copolymers of poly(oxyethylene)-poly(oxypropylene)-poly(oxyethylene) and derivatives thereof is disclosed in commonly owned U.S. 2010/0140141, which is hereby incorporated by references in its entirety.

The novel α,ω-bifunctionalized block copolymers with tertiary amines (aliphatics and aromatics), is shown in the equations (1) to (5):

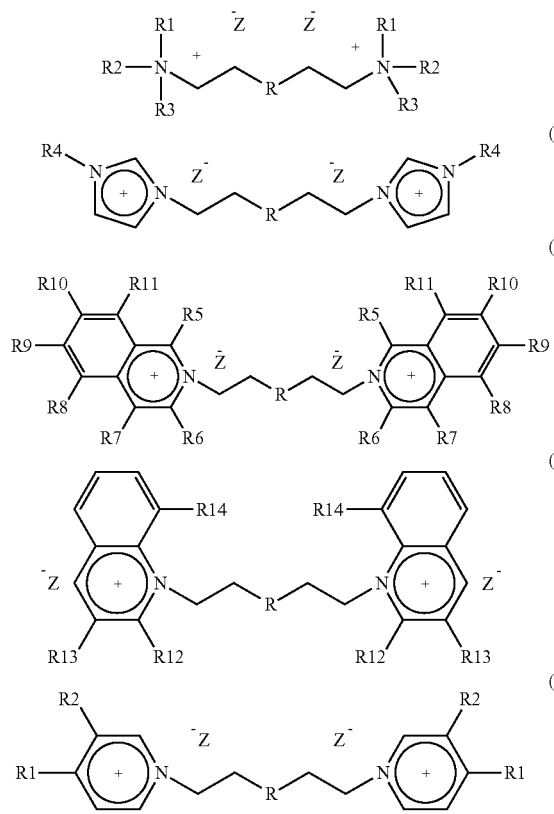

where R is

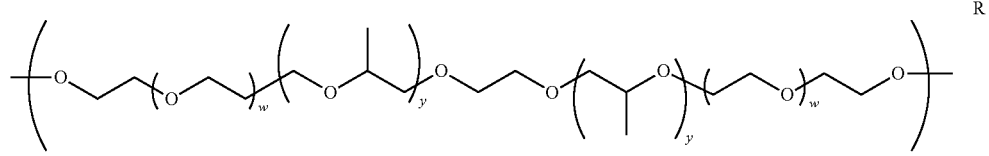

and where:

R represents triblock copolymers with a molecular weight ranging between 1000 and 4000 Daltons, of poly(oxyethylene)$_w$-poly(oxypropylene)$_y$-poly(oxyethylene)$_w$. The poly(oxyethylene)$_w$-poly(oxypropylene)$_y$-poly(oxyethylene)$_w$ as the starting material is preferably obtained using ethyleneglycol as an initiator.

w and y are numbers ranging between of 10 to 60, preferably between 15 to 55, even more preferably between 15 and 50.

$R_1$, $R_2$ and $R_3$ are independently radicals selected from the group consisting of —$CH_2(CH_2)_4B$; —CEGJ; —$CH_2CHLM$; —$CH_2(CH_2)_QM$;

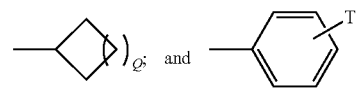

where A is a number between 1 and 19, B is H.

EGJ are independently radicals represented by: H, methyl, ethyl, n-propyl, iso-propyl, sec-butyl, iso-butyl, tert-butyl, n-butyl, phenyl, cyclohexyl, cyclopentyl.

L is a radical represented by methyl and ethyl and M is a hydroxyl group, Q is a number between 1 and 5; T is represented by the EGJ groups and $NO_2$, Cl, F, Br.

$R_4$ is independently a radical represented by —$(CH_2)_4B$; —OU; —$CH(C_6H_5)_2$; —$C(C_6H_5)_3$, where A is a number between 1 and 19, B is H; U is independently a radical represented by methyl, ethyl, and benzyl.

$R_5$ is independently a radical represented by -2(methyl-phenyl), -(4-methyl-phenyl), -(4-phenyl-phenyl); $R_6$ is independently a radical represented by -(4-methoxy-phenyl), -(4-piperazinyl), $NO_2$; $R_7$ is independently a radical represented by Br, (phenyl-sulfanyl), (methyl-sulfanyl); $R_8$ is independently a radical represented by $NO_2$ and bromide: $R_9$ is independently a radical represented by Br; $R_{10}$ is independently a radical represented by (-octyloxy-); $R_{11}$ is independently a radical represented by Br; $R_{12}$ is independently a radical represented by -methyl, -(4-methyl-phenyl), -(2-methoxy-phenyl); $R_{13}$ is a radical represented by $NO_2$, -(4-methyl-phenyl), -(3-methyl-phenyl), -(2-methyl-phenyl), -(2-methoxy-phenyl), -(3-methoxy-phenyl); $R_{14}$ is a radical represented by -methyl, -(2-phenoxy-ethoxy), -(4-nitro-phenoxy), -(4-phenoxy-butoxy).

Z is independently a radical represented by methansulfonate, benzensulfonate and para-toluenesulfonate.

The preferred amines of the present invention for producing the block copolymers are: dibutylhexadecylamine, tri-isooctylamine, trioctylamine, 2-ethyl-N,N-bis(2-ethyl-hexyl)-hexylamine, dimethyl-docosyl-amine, N,N-dimethyl-hexadecylamine, trihexylamine, 1-benzyl-1H-imidazole, 1-methyl-1H-imidazole, 1-pentyl-1H-imidazole, 1-butyl-1H-imidazole, 1-vinyl-1H-imidazole, 1-ethyl-1H-imidazole, 1-lauryl-1H-imidazol, 1-cyano-1H-imidazol, 1-hexyl-1H-imidazole, 1-propyl-1H-imidazole, 1-benzyloxy-1H-imidazole, 1-ethoxy-1H-imidazole, 1-methoxy-1H-imidazole, 1-methoxymethyl-1H-imidazole, 1-benzhydryl-1H-imidazole, 1-(diethoxymethyl)-1H-imidazole, 1-(triphenylmethyl)-1H-imidazole, 1-(2-methyl-phenyl)-isoquinoline, 1-(4-methyl-phenyl)-isoquinoline, 1-(4-phenyl-phenyl)-isoquinoline, 3-(4-methoxy-phenyl)-isoquinoline, 3-(4-piperazinyl)-isoquinoline, 3-nitro-isoquinoline, 4-bromo-isoquinoline, 4-phenyl-sulfanyl-isoquinoline, 4-methyl-sulfanyl-isoquinoline, 5-nitro-isoquinoline, 5-bromo-isoquinoline, 6-bromo-isoquinoline, 7-octyloxy-isoquinoline, 5,8-dibromo-isoquinoline, quinoline, 8-(2-phenoxy-ethoxy)-quinoline, 2,8-dimethyl-quinoline, 3-nitroquinoline, 3-(3-methyl-phenyl)-quinoline, 3-(2-methyl-phenyl)-quinoline, 3-(4methoxy-phenyl)-quinoline, 3-(3-methoxy-phenyl)-quinoline, 3-(2-methoxy-phenyl)-quinoline, 2-(benzyloxy)-quinoline, 2-(4-methyl-phenyl)-quinoline, 2-(2-methoxy-phenyl)-quinoline, 8-(4-nitro-phenoxy)-quinoline, 8-(4-phenoxy-butoxy)-quinoline, 2,8-dimethyl-quinoline, 3,4-dimethyl-pyridine, 4-(4-nitro-phenyl)-pyridine, pyridine, 3-(4-bromo-phenyl)-pyridine, 3-(4-nitro-phenyl)-pyridine, and 4-(cyclohexyl-methyl)-pyridine.

Examples of particularly preferred copolymers include:
α,ω-di-aryl or alkyl sulfonates of PEO-PPO-PEO of bis-ammonium, where the aliphatic amines can be linear or branched, functionalized or unfunctionalized aliphatic groups, α,ω-di-aryl or alkyl sulfonates of PEO-PPO-PEO of bis-ammonium, where the aromatic amines are derivatives of 1H-alkyl-imidazole, 1H-aryl-imidazole, 1H-alkyl-functionalized-imidazole and 1H-aryl-functionalized-imidazole, α,ω-di-aryl or alkyl sulfonates of PEO-PPO-PEO of bis-isoquinolinium, where the aromatic amines are derivatives of isoquinoline that can be functionalized or unfunctionalized, α,ω-di-aryl or alkyl sulfonates of PEO-PPO-PEO of bis-quinolinium, where the aromatic amines are derivatives of quinolone that can be functionalized or unfunctionalized, α,ω-di-aryl or alkyl sulfonates of PEO-PPO-PEO of bis-pyridinium, where the aromatic amines are derivatives of pyridine can be functionalized or unfunctionalized.

SYNTHESIS OF FUNCTIONALIZED BLOCK COPOLYMERS

The experimental procedure earlier mentioned was described widely in previous applications U.S. 2010/0140141 and MX/2008/015156; the present invention is distinguished from previous processes because the nucleophilic substitution is carried out with tertiary amines (aliphatic and aromatic) according to the present invention.

The following is a detailed description of one embodiment of the present invention.
Nucleophilic substitution of the α,ω-alkyl and aryl sulfonates of the block copolymers poly(ethylene oxide)-poly(propylene oxide)-poly(ethylene oxide) with tertiary amines)

10 mmoles of the copolymer α,ω-dialkyl-sulfonate-ester or α,ω-diaryl-sulfonate-ester of poly(ethylene oxide)$_w$-poly(propylene oxide)$_y$-poly(ethylene oxide)$_w$. (Mn=2200-2500 g/mole, I=1.12) and 50 mL of toluene were put in a bottom rounded flask with three necks, magnetic stirrer, condenser and addition funnel. Afterwards, 10.2 mmole of the aliphatic or aromatic tertiary amine dissolved in toluene were slowly added to the copolymer, keeping the temperature between 30 and 35° C. and submitted to a reflux heating for 17 hours. After this time, the solvent was eliminated at reduced pressure.

Once the copolymers were obtained, they were submitted to characterization using the following instrumental methods:

1.—Spectrometer of Fourier transform infrared Brucker® tensor model 27, employing ATR method with OPUS® software.

2.—Spectrometer of nuclear magnetic resonance Varian® model BB at 200 MHz to obtain $^1$H and 50 MHz $^{13}$C spectra, employing deuterated chloroform and deuterated dimethylsulfoxide as solvents. The signal shifts are given in parts per million (δ) referred to the tetramethylsilane (TMS) as internal standard.

3.—Size exclusion chromatograph (SEC) of Agilent® model 1100, furnished with PlegI column and using tetrahydrofurane (THF) as eluent, used to determine the distribution of the copolymers molecular weights and polydispersity(I).

TABLE NO. 1

Molecular mass number averages (Mn) and polydispersity index (I) of poly(ethylene oxide)$_w$-poly(propylene oxide)$_y$-poly(ethylene oxide)$_w$, (POE-POP-POE) copolymers prepared using potassium ethylene glycolate as initiator.

| Copolymer | Mn (g/mole) | I | Physical state |
|---|---|---|---|
| A | 4000 | 1.15 | Solid |
| B | 4000 | 1.12 | Viscous liquid |
| C | 2900 | 1.17 | Viscous liquid |
| D | 2700 | 1.11 | Viscous liquid |
| E | 2400 | 1.12 | Viscous liquid |
| F | 1700 | 1.14 | Viscous liquid |
| G | 1350 | 1.15 | Viscous liquid |

Where:
A, B, C, D, E, F, and G are poly(ethylene oxide)$_w$-poly(propylene oxide)$_y$-poly(ethylene oxide)$_w$, (POE$_w$-POP$_y$-POE$_w$) copolymers, which exhibit different molecular weight number averages and polydispersity index, so they were labeled with letters A to G.

The spectroscopic characterization of some bifunctionalized copolymers is now depicted. These examples are illustrative but not limiting:

(IMP-CF23H) α,ω-di-para-toluensulfonate of poly(ethylene oxide)$_w$-poly(propylene oxide)$_y$-poly(ethylene oxide)$_w$ of bis-tri-octyl-ammonium: viscous liquid; I.R. ν cm$^{-1}$: 2978, 2953, 2870, 2790, 1595, 1459, 1383, 1354, 1174, 1100, 1069, 977, 825, 775, 752; $^{13}$C NMR (DMSO-d$_6$): 13.9, 17.1, 21.6, 21.2, 21.8, 25.7, 25.8, 42.7, 60.5, 60.7, 63.2, 70.2, 70.5, 72.9, 73.5, 75.1, 75.4, 75.7, 127.9, 130.0, 132.7, 145.1.

(IMP-CF24H) α,ω-di-benzensulfonate of poly(ethylene oxide)$_w$-poly(propylene oxide)$_y$-poly(ethylene oxide)$_w$ of bis-tri-hexyl-ammonium: viscous liquid; I.R. ν cm$^{-1}$: 2975, 2948, 2865, 2790, 1595, 1459, 1383, 1354, 1172, 1100, 1069, 975, 825, 775, 751; $^{13}$C NMR (DMSO-d$_6$): 14.0, 17.1, 22.5, 25.7, 27.0, 42.6, 60.6, 60.7, 63.2, 70.2, 70.5, 72.9, 73.5, 75.1, 75.4, 75.7, 127.9, 129.41, 134.6, 135.1.

(IMP-CF25H) α,ω-di-benzensulfonate of poly(ethylene oxide)$_w$-poly(propylene oxide)$_y$-poly(ethylene oxide)$_w$ of bis-1H-methyl-imidazolium: viscous liquid; I.R. ν cm$^{-1}$: 3049, 2930, 2858, 1571, 1468, 1385, 1170, 1102, 1018, 895, 767, 655 $^{13}$C NMR (DMSO-d$_6$): 17.2, 36.2, 42.8, 60.6, 60.8, 63.1, 70.2, 70.4, 72.8, 75.1, 75.5, 75.7, 121.9, 123.7, 129.4, 134.5, 135.2, 137.6.

(IMP-CF26H) α,ω-di-benzensulfonate of poly(ethylene oxide)$_w$-poly(propylene oxide)$_y$-poly(ethylene oxide)$_w$ of bis-1H-butyl-imidazolium: viscous liquid; I.R. ν cm$^{-1}$: 3052, 2945, 2863, 1565, 1465, 1380, 1165, 1102, 1018, 896, 765, 655; $^{13}$C NMR (DMSO-d$_6$): 15.5, 17.2, 22.3, 31.0, 36.2, 45.1, 60.6, 60.8, 63.1, 70.2, 70.4, 72.8, 75.1, 75.5, 75.7, 122.1, 123.6, 127.4, 129.2, 133.5, 136.2, 137.6.

(IMP-CF27H) α,ω-di-benzensulfonate of poly(ethylene oxide)$_w$-poly(propylene oxide)$_y$-poly(ethylene oxide)$_w$ of bis-isochinolinium: viscous liquid; I.R. ν cm$^{-1}$: 3023, 2971, 2965, 2856, 1641, 1607; 1583, 1526, 1482, 1470, 1390, 1177, 1173, 1165, 1112, 1105, 983, 946, 819, 759; $^{13}$C NMR (DMSO-d$_6$): 17.1, 46.1, 60.4, 60.7, 64.1, 70.3, 70.4, 72.9, 75.2, 75.3, 75.7, 126.4, 127.1, 127.8, 128.0, 129.4, 131.2, 134.0, 134.5, 135.2, 137.0, 137.3, 150.2.

(IMP-CF28H) α,ω-di-benzensulfonate of poly(ethylene oxide)$_w$-poly(propylene oxide)$_y$-poly(ethylene oxide)$_w$ of bis-chinolinium: viscous liquid; I.R. ν cm$^{-1}$: 3056, 3024, 2950, 2921, 2865, 2728, 1624, 1598, 1590, 1525, 1466, 1407, 1383, 1276, 1209, 1175, 1165, 1153, 1134, 1105, 989, 875, 801, 777, 771; $^{13}$C NMR (DMSO-d$_6$): 17.2, 45.8, 60.4, 60.7, 64.1, 70.3, 70.4, 72.9, 75.2, 75.3, 75.7, 118.9, 122.2, 127.8, 129.3, 129.7, 129.80, 130.7, 135.1, 135.2, 137.3, 147.2, 149.5.

(IMP-CF29H) α,ω-di-benzensulfonate of poly(ethylene oxide)$_w$-poly(propylene oxide)$_y$-poly(ethylene oxide)$_w$ of bis-pyridinium: viscous liquid; I.R. ν cm$^{-1}$:3068, 3010, 2970, 2960, 2850, 1633, 1620, 1598, 1482, 1436, 1388, 1275, 1217, 1174, 1162, 1108, 980, 872, 750; $^{13}$C NMR (DMSO-d$_6$): 17.1, 45.9, 60.4, 60.9, 64.0, 70.3, 70.4, 72.9, 75.2, 75.2, 75.7, 127.4, 128.0, 129.6, 134.1, 135.2, 142.1, 146.0.

A second feature of the present invention is directed to the preparation of dewatering and desalting agents and formulations based on poly(ethylene oxide)$_w$-poly(propylene oxide)$_y$-poly(ethylene oxide)$_w$ block copolymers α,ω-bifunctionalized with tertiary amines (aliphatics and aromatics), using solvents with boiling point between 35 to 200° C., preferably dichloromethane, chloroform, benzene, toluene, xylenes, turbosine, naphtha, individually or mixtures thereof. Prepared solutions include amounts ranging from 100 ppm (0.01 wt. %) to 50000 ppm (5 wt. %) of the copolymers.

A third feature of the present invention is relates to the application of the prepared solutions in methods for dehydrating and desalting agents of crude oils with gravities ranging between 14-23° API, by adding small volumes of dissolution or formulation and avoiding the solvent effect influenced on the emulsion breaking.

Individual and Prepared Composition Evaluation from the Block Copolymer α,ω-Bifunctionalized with Tertiary Amines Aliphatic and Aromatics, as Dehydrating and Desalting Agents on Crude Oils with API Gravities Ranging Between 14-23° API.

Different concentrated dissolutions and formulations were prepared for each of the bifunctionalized copolymers from 5 to 40% by weight, employing disolvents with boiling point is ranging from 35 to 200° C., preferably dichloromethane, chloroform, benzene, toluene, xylenes, turbosine, naphtha, individually or in mixtures thereof, and adding small volumes of the dissolution to avoid the solvent effect influenced on the emulsion breaking. Block copolymers bifunctionalized were prepared in concentrations of 100 to 50000 ppm.

Three crude oils identified as CM1, CM2 and CM3 used in this evaluation were characterized as is shown following:

TABLE NO. 2

Physicochemistry characterization of crude oils

| Test | CM1 | CM2 | CM3 |
|---|---|---|---|
| API gravity | 14.9 | 19.3 | 22.2 |
| Sal content (lbs/1000ls) | 10870 | 248 | 7050 |
| Paraffin (wt. %) | 4.4 | 3.6 | 3.7 |
| Distilled water (vol. %) | 26.0 | 20 | 13.0 |
| Water/sediment (vol. %) | 24.7 | 19 | 12.6 |
| Runoff Temperature (° C.) | −18 | −30 | −24 |
| Kinematic viscosity (mm$^2$/s) | 2302 | 343 | 1161.4 |
| Heptane Insoluble (wt. %) | 10.2 | 10.8 | 7.7 |
| Saturated (wt. %) | 11.8 | 20.7 | 13.9 |
| Aromatics (wt. %) | 31.7 | 26.8 | 39.7 |
| Resins (wt. %) | 45.7 | 43.4 | 39.1 |
| Asphaltenes (wt. %) | 10.8 | 9.1 | 7.3 |
| MW Cryoscopy (g/mole) | 511 | 370 | 374 |
| CII | 0.296 | 0.424 | 0.274 |

Evaluation procedure was described in detail in U.S. 2010/0140141 and U.S. 2012/026312, which are hereby incorporated by reference in their entirety. Then and by way of demonstration that involves no limitation, it shows the graphic results, in the concentration intervals applied ranging from 100 ppm to 1200 ppm.

Figure 2:
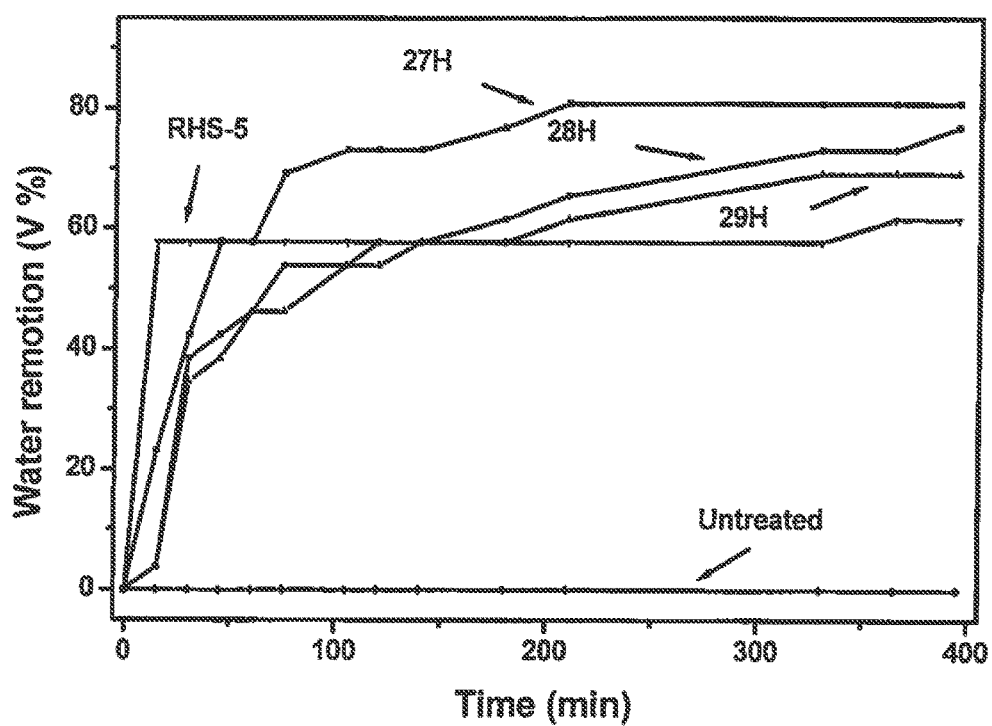
FIG. 2 is a graph showing the demulsifying activity of (27H-29H) triblock copolymers α,ω-bifunctionalized with tertiary amines, on CM1 crude oil at 80° C. and 600 ppm.

From FIGS. 1 and 2 (application concentration 600 ppm on CM1 crude oil), it observes that IMP-CF26H, IMP-CF27H, and IMP-CF28H bifunctionalized copolymers are able to break up the emulsion with high yields giving 84% (390 minutes), 81% (210 minutes), and 77% (390 minutes), respectively; whereas the formulation IMP-RHS5 (25 minutes) breaks up very quickly then stays stable in efficiency 58%.

Figure 3:
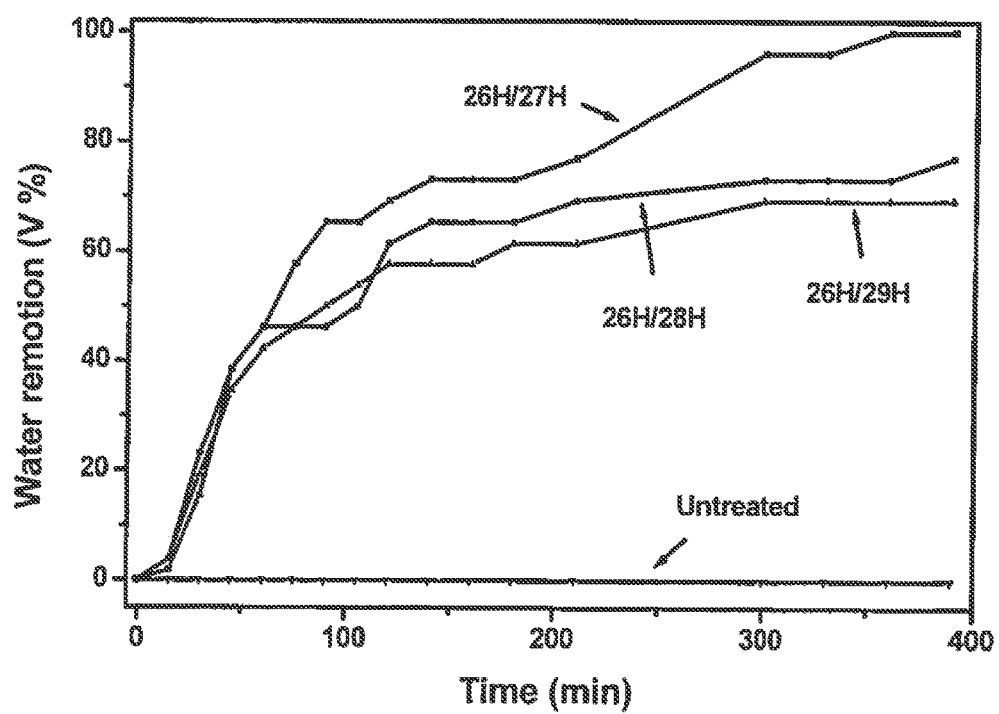
FIG. 3 is a graph showing the demulsifying activity of (26H to 27H-29H) (300 ppm/300 ppm) formulation of triblock copolymers of α,ω-bifunctionalized with tertiary amines on CM1 crude oil at 80° C.

Continuing with CM1 crude oil, shown in FIG. 3 that IMP-CF 26H/IMP-CF 27H (300 ppm/300 ppm) composition reached 100% of yield on the emulsion breaking at 360 minutes of treatment, therefore, there is a synergy between these two copolymers, because individually (600 ppm) only reached 84% and 81% of yield on the emulsion breaking.

Figure 4:
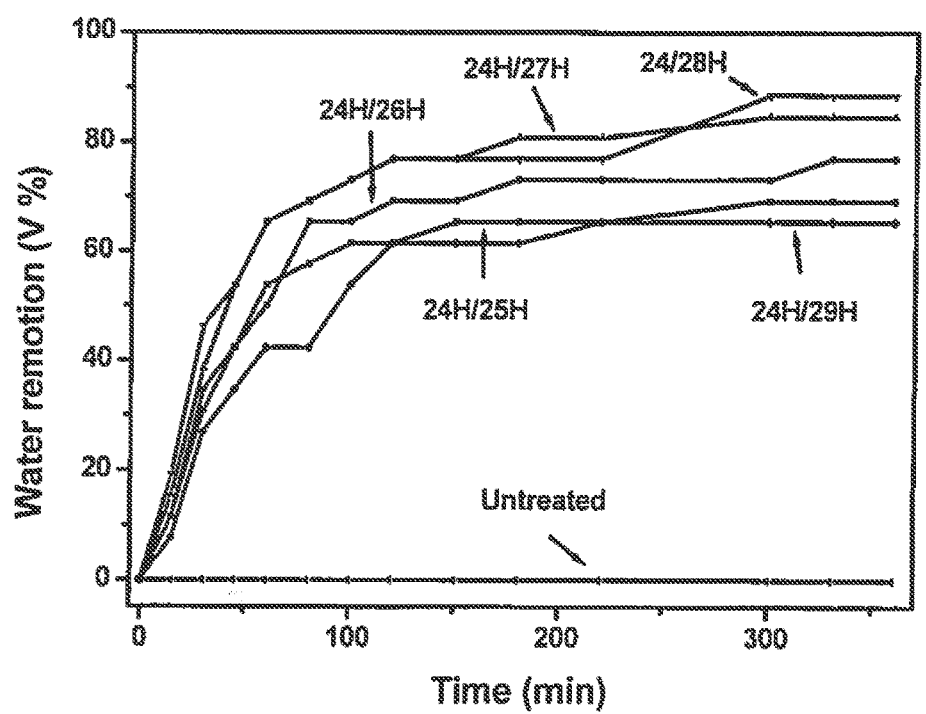
FIG. 4 is a graph showing the demulsifying activity of compositions of (24H to 25H-29H) (300 ppm/300 ppm) triblock copolymers of α,ω-bifunctionalized with tertiary amines on CM1 crude oil at 80° C.
Figure 5:
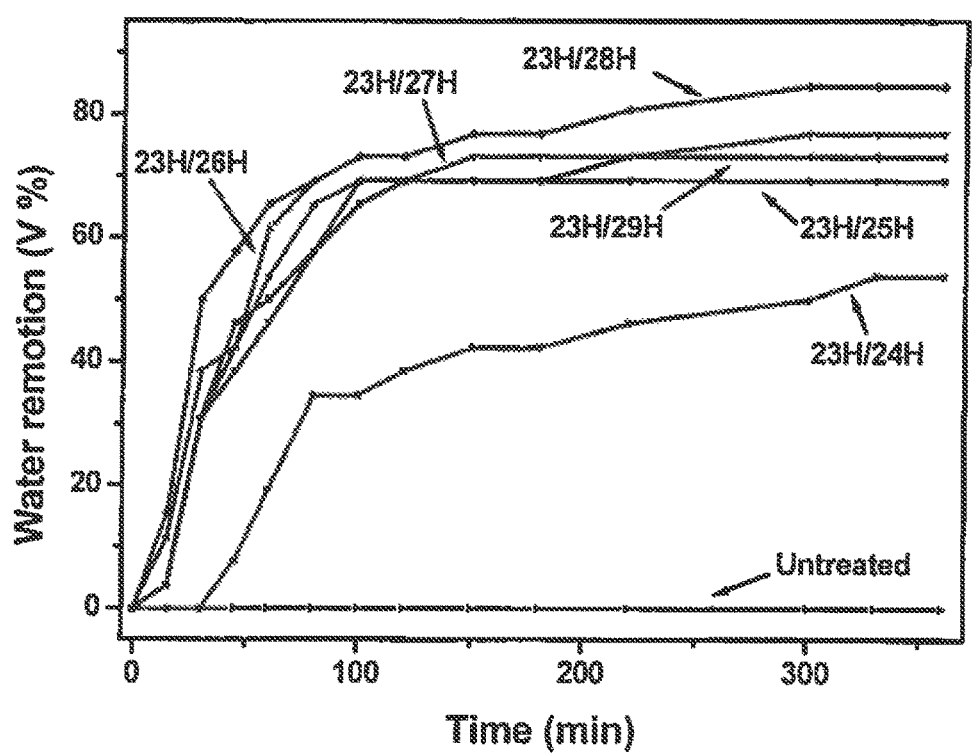
FIG. 5 is a graph showing the demulsifying activity of compositions of (23H to 24H-29H) (300 ppm/300 ppm) triblock copolymers of α,ω-bifunctionalized with tertiary amines on CM1 crude oil at 80° C.

In FIG. 4, it is observed that the best composition is IMP-CF 24H/IMP-CF 28H (89%, 300 minutes) and IMP-CF24H/IMP-CF27H with 85% of efficiency at 300 minutes of treatment; whereas in FIG. 5 is observed that IMP-CF23H/IMP-CF28H and IMP-CF23H/IMP-CF26H compositions are able to break up the emulsion with 85% of yield at 300 minutes, all these formulations were applied on CM1 crude oil in concentration of 300 ppm/300 ppm, and to overcome the efficiency of the novel evaluated copolymers individually, again it observes that there exists a synergy with this novel kind of copolymers.

Figure 6:
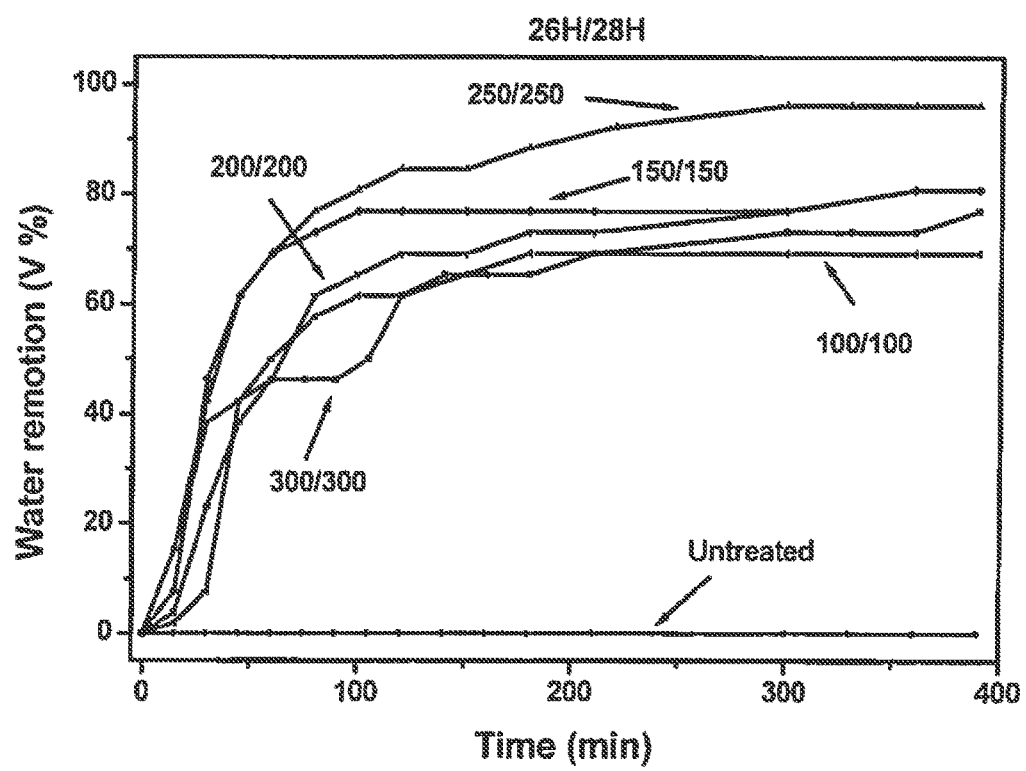
FIG. 6 is a graph showing the demulsifying activity of compositions of (26H/28H) triblock copolymers of α,ω-bifunctionalized with tertiary amines on crude oil CM1 at 80° C.

In FIG. 6 (CM1 crude oil), in the left side, it is represented the emulsion breaking efficiency using the IMP-CF26H/IMP-CF28H composition in different concentrations, the best of all is 250 ppm/250 ppm, giving 96% at 5 hours, showing that exists major synergism at low concentration, thus the formulation of 300 ppm/300 ppm breaks up the emulsion at 390 minutes with an efficiency of 78%.

Figure 7:
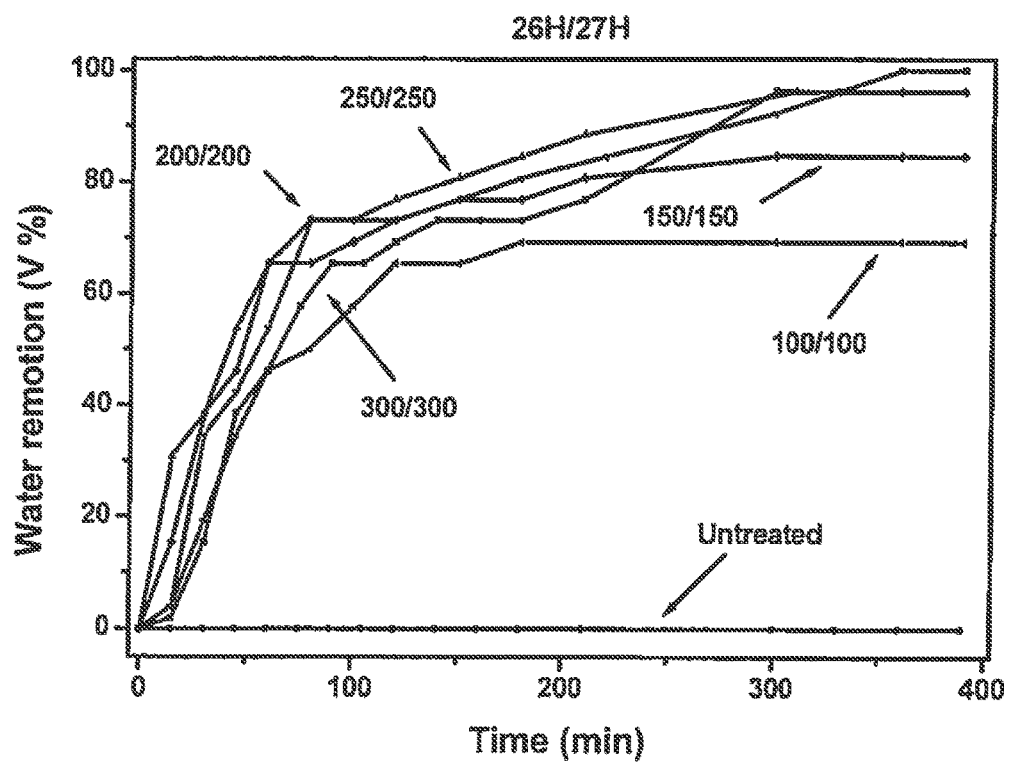
FIG. 7 is a graph showing the demulsifying activity of compositions of (26H/27H) triblock copolymers of α,ω-bifunctionalized with tertiary amines on CM1 crude oil at 80° C.

On the right side of the same FIG. 7, the efficiency of the IMP-CF26H/IMP-CF27H composition, at 300 ppm/300 ppm, shows 100% of rupture, whereas the concentrations of 250/250 and 200/200 ppm/ppm reached 96% of the emulsion breaking in the same time. The range of concentrations applied in both compositions ranging from 100 ppm/100 ppm to 300 ppm/300 ppm.

TABLE NO. 3

Efficiency in the crude desalting CM1 with different compositions.

| Composition | ppm/ppm | Dehydrated % | Time[1] | Salt Remains[2] | Desalted % |
|---|---|---|---|---|---|
| IMP-CF26H/IMP-CF 27H | 300/300 | 100 | 360 | 2600 | 76.0 |
| IMP-CF26H/IMP-CF27H | 250/250 | 96 | 300 | 2850 | 73.8 |
| IMP-CF26H/IMP-CF27H | 200/200 | 96 | 300 | 2475 | 77.2 |
| IMP-CF26H/IMP-CF28H | 250/250 | 96 | 300 | 1010 | 90.7 |

[1](minutes),
[2](lbs/1000 barrels)

Desalted data shown in Table No. 3 indicate that the highest percentage (907%) was achieved with the IMP-CF26H/IMP-CF28H (250 ppm/250 ppm) composition, other compositions have similar values.

Figure 8:
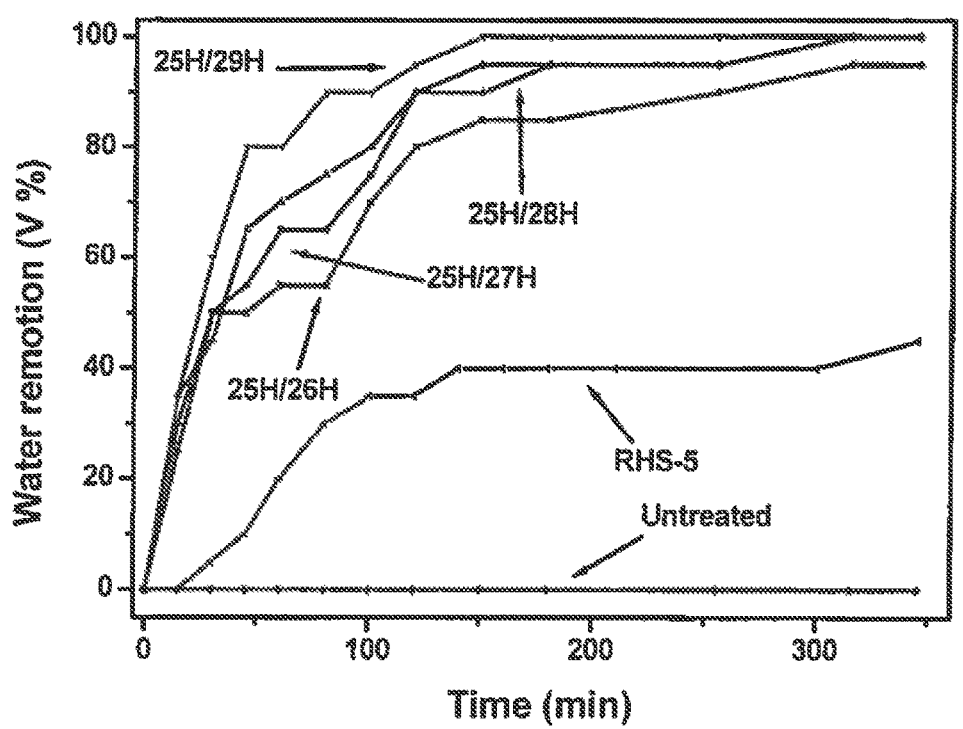
FIG. 8 is a graph showing the demulsifying activity of compositions of (25H to 26H-29H) (300 ppm/300 ppm) triblock copolymers in α,ω-bifunctionalized with tertiary amines and IMP-RHS5 formulation at 600 ppm on CM2 crude oil at 80° C.
Figure 9:
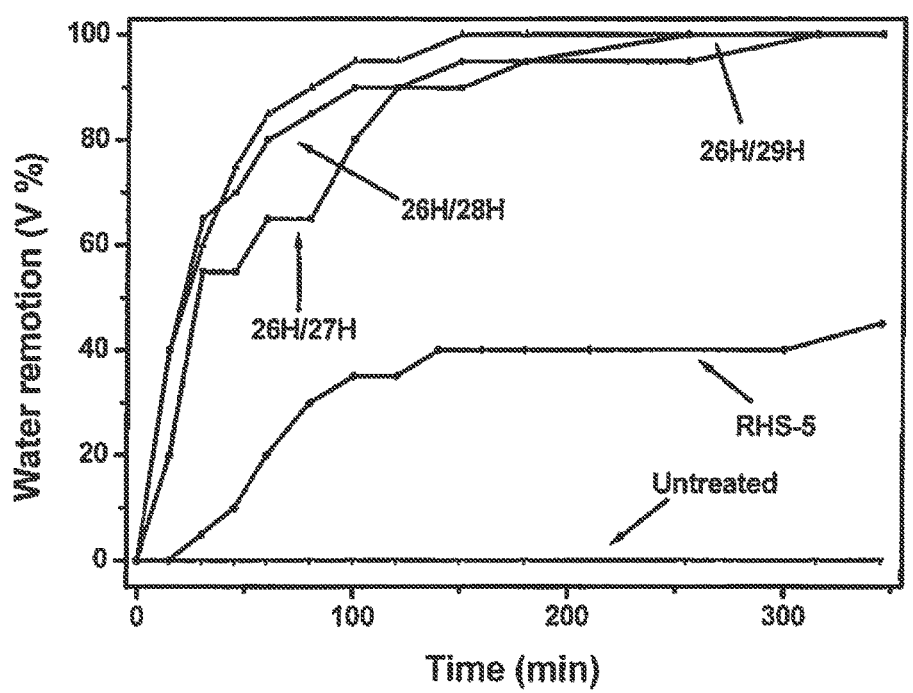
FIG. 9 is a graph showing the demulsifying activity of compositions of (26H to 27H-29H) (300 ppm/300 ppm) triblock copolymers in α,ω-bifunctionalized with tertiary amines and IMP-RHS5 formulation at 600 ppm on CM2 crude oil at 80° C.

FIG. 8 shows the results of the formulations prepared from the IMP-CF25H/IMP-CF29H and IMP-CF25H/IMP28H copolymers which breaks the 100% of the water-in-oil emulsion, in 150 minutes and 320 minutes, respectively when they are applied over CM2 crude oil; whereas FIG. 9 clearly shows that the best compositions were IMP-CF26H/IMP-CF29H and IMP-CF26H/IMP-CF28H, both formulations achieved 100% of rupture at 150 minutes and 260 minutes respectively.

Figure 10:
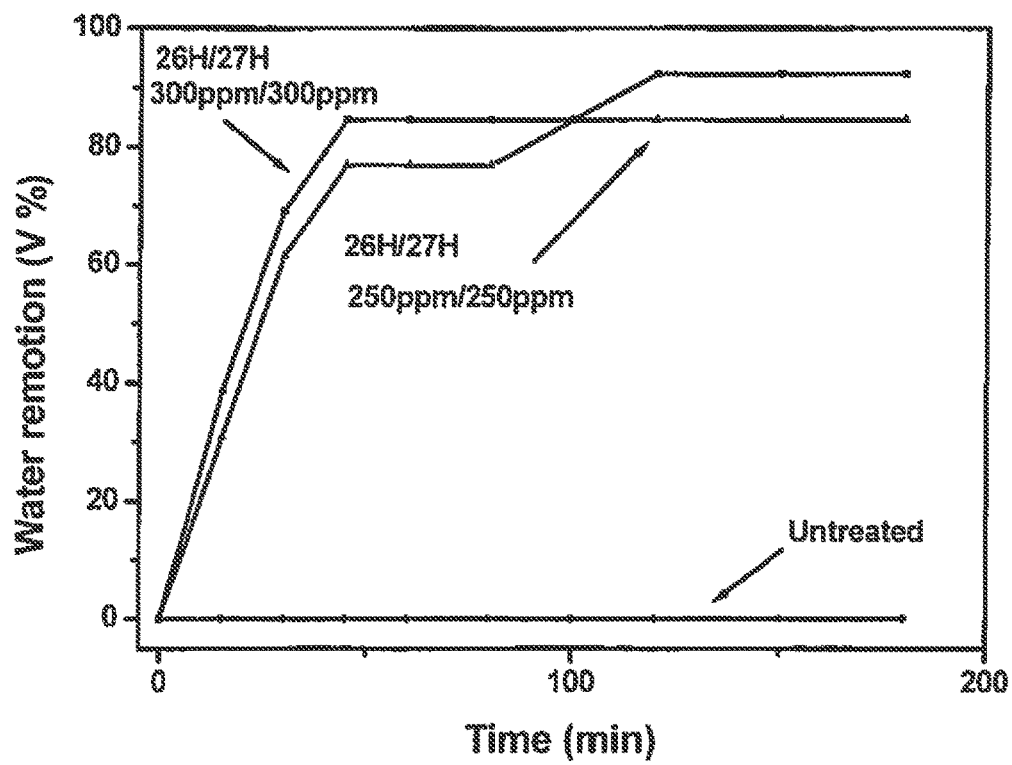
FIG. 10 is a graph showing the demulsifying activity of compositions of (26H/27H) triblock copolymers based on α,ω-bifunctionalized with tertiary amines and the IMP-RHS5 commercial formulation on CM3 crude oil at 80° C.

FIG. 10 (Crude oil CM3) shows that the best composition is composed by IMP-CF26H/IMP-CF27H 300 ppm/300 ppm compared to IMP-CF26H/IMP-CF27H, which reach the emulsion breaking at 120 minutes with an efficiency of 92%.

TABLE NO. 4

Efficiency of desalting process in the CM3crude oil with different compositions

| Composition | ppm/ppm | Dehydrated % | Time[1] | Salt Remains[2] | Desalted % |
|---|---|---|---|---|---|
| IMP-CF26H/IMP-CF27H | 300/300 | 92 | 120 | 2475 | 65.0 |
| IMP-CF26H/IMP-CF27H | 250/250 | 86 | 100 | 2600 | 63.1 |

[1](minutes),
[2](lbs/1000 barrels)

The results of Table No. 4 indicate that the higher dehydration percentage the greater desalting percentage.

Thus, the compositions prepared from the block copolymers bifunctionalized with tertiary amines of this invention together with the block copolymers bifunctionalized with secondary amines are more effective in the dehydrated and desalted of Mexican crude oils than the IMP-RHS-5 commercial formulation.

What is claimed is:

1. A method of dewatering and desalting crude oil, comprising:

mixing a dewatering and desalting agent and a crude oil having a specific gravity of about 14 to 23° API at a concentration of at least 100 ppm, wherein said dewatering and desalting agent comprises at least one compound selected from the group consisting of Formula 1 and Formula 5;

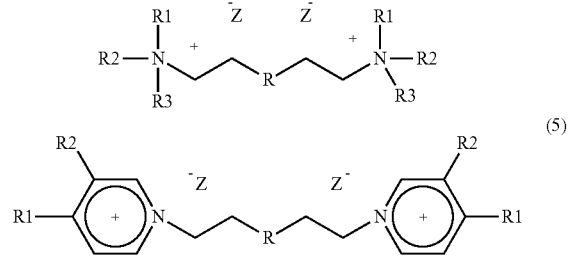

where R is

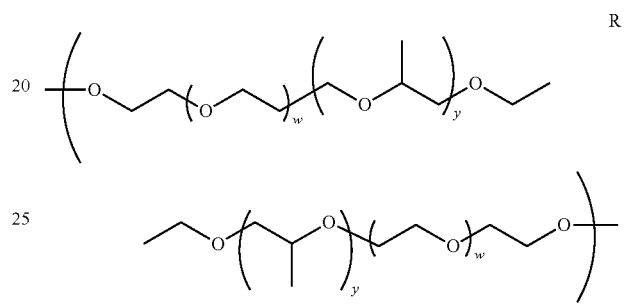

and R represents a copolymer with a molecular weight in the range from 1000 to 4000 Daltons, w and v are independently a whole number consistent with the molecular weight, $R_1$, $R_2$ and $R_3$ radicals are independently selected from the group consisting of —$CH_2(CH_2)_4B$; —CEGJ; —$CH_2CHLM$; —$CH_2(CH_2)_QM$;

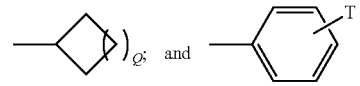

where A is a number between 1 and 9, B is H,

E, G and J are a radical independently selected from the group consisting of:—H, methyl, ethyl, n-propyl, iso-propyl, sec-butyl, iso-butyl, tert-butyl, n-butyl, phenyl, cyclohexyl, and cyclopentyl, L is a radical represented by methyl or ethyl, and M is a hydroxyl group, O is a number between 1 and 5, T is represented by groups E, G and J, $NO_2$, Cl, F and Br; and Z is a radical independently selected from the group consisting of methanesulfonate, benzenesulfonate and para-toluenesulfonate.

2. The method of claim 1, wherein said copolymer is a mixture in a solvent having a boiling point of about 35° C. to about 200° C., said method comprising adding said mixture to the crude oil.

3. The method of claim 2, wherein said solvent is selected from the group consisting of dichloromethane, chloroform, benzene, toluene, xylene, turbosine, naphtha and mixtures thereof, and where said mixture is added in an amount of 0.01% to 5% by weight.

4. The method of claim 1, wherein
said dewatering and desalting agent comprises a mixture of two of said copolymers in a ratio of about 1:1 to said crude oil.

5. The method of claim 1, wherein
said dewatering and desalting agent comprises a mixture of a copolymer of Formula 1 and at least one copolymer of Formula 5.

\* \* \* \* \*